(12) United States Patent
Moon et al.

(10) Patent No.: US 10,337,030 B2
(45) Date of Patent: Jul. 2, 2019

(54) MICROBIALLY-MEDIATED METHOD FOR SYNTHESIS OF METAL CHALCOGENIDE NANOPARTICLES

(71) Applicants: UT-Battelle, LLC, Oak Ridge, TN (US); U.S. Geological Survey, Reston, VA (US)

(72) Inventors: Ji Won Moon, Oak Ridge, TN (US); Tommy Joe Phelps, Knoxville, TN (US); Ronald Oremland, Brisbane, CA (US); David E. Graham, Knoxville, TN (US); Ilia N. Ivanov, Knoxville, TN (US); Christopher B. Jacobs, Knoxville, TN (US); Gyoung Gug Jang, Knoxville, TN (US); Michelle K. Kidder, Clinton, TN (US); Pooran C. Joshi, Knoxville, TN (US); Beth L. Armstrong, Clinton, TN (US)

(73) Assignees: UT-Battelle, LLC, Oak Ridge, TN (US); U.S. Geological Survey, Reston, VA (US)

( * ) Notice: Subject to any disclaimer, the term of this patent is extended or adjusted under 35 U.S.C. 154(b) by 0 days.

(21) Appl. No.: 15/643,610

(22) Filed: Jul. 7, 2017

(65) Prior Publication Data

US 2018/0010153 A1 Jan. 11, 2018

Related U.S. Application Data

(60) Provisional application No. 62/359,356, filed on Jul. 7, 2016.

(51) Int. Cl.
*C12P 3/00* (2006.01)
*B82Y 40/00* (2011.01)
*C01B 19/00* (2006.01)

(52) U.S. Cl.
CPC ............. *C12P 3/00* (2013.01); *B82Y 40/00* (2013.01); *C01B 19/002* (2013.01)

(58) Field of Classification Search
None
See application file for complete search history.

(56) References Cited

U.S. PATENT DOCUMENTS 5,271,831 A * 12/1993 Oremland ............ C01B 19/02
210/170.08
2005/0013759 A1 * 1/2005 Grow .................... B82Y 30/00
423/263

(Continued)

OTHER PUBLICATIONS

Mal, J. et al., "Metal chalcogenide quantum dots: biotechnological synthesis and applications", Royal Society of Chemistry Advances, (Apr. 13, 2016), vol. 6, pp. 41477-41495.

(Continued)

*Primary Examiner* — Sheng H Davis
(74) *Attorney, Agent, or Firm* — Scully, Scott, Murphy & Presser, P.C.

(57) ABSTRACT

A method for producing metal chalcogenide nanoparticles, the method comprising: (i) producing hydrogen chalcogenide-containing vapor from a microbial source, wherein said microbial source comprises: (a) chalcogen-reducing microbes capable of producing hydrogen chalcogenide vapor from a chalcogen-containing source; (b) a culture medium suitable for sustaining said chalcogen-reducing microbes; (c) at least one chalcogen-containing compound that can be converted to hydrogen chalcogenide vapor by said chalcogen-reducing microbes; and (d) at least one nutritive compound that provides donatable electrons to said chalcogen-reducing microbes during consumption of the nutritive compound by said chalcogen-reducing microbes; and (ii) directing said hydrogen chalcogenide-containing vapor into a metal-containing solution comprising a metal (Continued)

salt dissolved in a solvent to produce metal chalcogenide nanoparticles in said solution, wherein said chalcogen is sulfur or selenium, and said chalcogenide is sulfide or selenide, respectively. The invention is also directed to metal chalcogenide nanoparticle compositions produced as above and having distinctive properties.

21 Claims, 5 Drawing Sheets

(56) References Cited

U.S. PATENT DOCUMENTS

| | | | |
|---|---|---|---|
| 2006/0014261 A1 | 1/2006 | Phelps et al. | |
| 2009/0071897 A1* | 3/2009 | Ollivier | C02F 3/345 |
| | | | 210/603 |
| 2010/0330367 A1* | 12/2010 | Phelps | C01B 17/20 |
| | | | 428/402 |
| 2011/0233487 A1 | 9/2011 | Hur et al. | |
| 2013/0164810 A1* | 6/2013 | Warkentin | C12P 3/00 |
| | | | 435/168 |
| 2014/0220654 A1 | 8/2014 | Phelps et al. | |

OTHER PUBLICATIONS

Pearce, C.I. et al., "Microbial manufacture of chalcogenide-based nanoparticles via the reduction of selenite using Veillonella atypica: an in situ EXAFS study", Nanotechnology, (Mar. 11, 2008). vol. 19, pp. 1-13.

International Search Report dated Sep. 13, 2017 issued in PCT/US2017/041010.

* cited by examiner

MICROBIALLY-MEDIATED METHOD FOR SYNTHESIS OF METAL CHALCOGENIDE NANOPARTICLES

CROSS REFERENCE TO RELATED APPLICATION

The present application claims benefit of U.S. Application No. 62/359,356 filed on Jul. 7, 2016, all of the contents of which are incorporated herein by reference.

STATEMENT REGARDING FEDERALLY SPONSORED RESEARCH

This invention was made with government support under Prime Contract No. DE-AC05-00OR22725 awarded by the U.S. Department of Energy. The government has certain rights in the invention.

FIELD OF THE INVENTION

The present invention relates to the field of microbial synthesis of inorganic materials, and more particularly, microbial synthesis of metal chalcogenide (e.g., metal sulfide or metal selenide) nanoparticles.

BACKGROUND OF THE INVENTION

Nanoparticles having metal non-oxide compositions (i.e., "semiconductor" or "quantum dot" nanoparticles) are increasingly being used in numerous emerging applications. Some of these applications include electronics (e.g., transistors and diode lasers), LED displays, photovoltaics (e.g., solar cells), and medical imaging. Quantum dot nanoparticles are also being investigated as powerful new computer processing elements (i.e., qubits). Semiconductor nanoparticles often possess a metal chalcogenide composition, such as CdS, CdSe, ZnS, and ZnSe.

As a consequence of its small size, the electron band structure of a quantum dot differs significantly from that of the bulk material. In particular, significantly more of the atoms in the quantum dot are on or near the surface, in contrast to the bulk material in which most of the atoms are far enough removed from the surface so that a normal band structure predominates. Thus, the electronic and optical properties of a quantum dot are related to its size. In particular, photoluminescence is size dependent.

Several physical methods are known for synthesizing semiconductor nanoparticles. Some of the physical techniques include advanced epitaxial, ion implantation, and lithographic techniques. The physical techniques are generally useful for producing minute amounts of semiconductor nanoparticles with well-defined (i.e., tailor-made, and typically, uniform) morphological, electronic, magnetic, or photonic characteristics. The physical techniques are typically not useful for synthesizing semiconductor nanoparticles in commercially significant quantities (e.g., grams or kilograms).

Several chemical processes are also known for the production of metal chalcogenide nanoparticles. Some of these methods include arrested precipitation in solution, synthesis in structured media, high temperature pyrolysis, and sonochemical methods. Although the foregoing chemical processes are generally capable of producing semiconductor nanoparticles in more significant quantities, the processes are generally energy intensive (e.g., by generally requiring heating and a post-annealing step), and hence, costly. Accordingly, commercially significant amounts of the resulting nanoparticles tend to be prohibitively expensive.

By some methods, commercial (bulk) hydrogen sulfide gas is bubbled into a solution containing a metal salt to produce metal sulfide particles. However, the bulk hydrogen sulfide process generally results in a significant proportion of the hydrogen sulfide being wasted to the atmosphere, which is not only costly but presents a significant health risk. Moreover, the bulk hydrogen sulfide process is generally not amenable to producing metal sulfide particles of a specific size. In particular, the bulk hydrogen sulfide process is generally substantially limited in its ability to produce nanoparticles in the lower nanoscale size range, e.g., below 100 nm.

The microbial synthesis of semiconductor nanoparticles is known. These processes are also referred to herein as "conventional nanofermentation" or "conventional NF". See, for example, P. R. Smith, et al., *J. Chem. Soc., Faraday Trans.*, 94(9), 1235-1241 (1998) and C. T. Dameron, et al., *Nature*, 338: 596-7, (1989). These processes are generally more capable of controlling the particle size and even shape or crystallinity of the resulting particles. However, there are significant obstacles that continue to hamper such microbially-mediated methods from being commercially viable. For example, current microbial methods are generally limited to the production of semiconductor nanoparticles on a small research scale. In addition, current microbial processes generally produce semiconductor nanoparticles that are contaminated with microbial components (e.g., cell membranes) or components in the culture medium necessary for sustaining the microbes. Accordingly, numerous separation and washing steps are generally required.

Moreover, as the conventional microbial process requires the microbes to be in contact with the metal ions to produce the semiconductor particles, the chemical and physical conditions used in producing the metal semiconductor nanoparticles are substantially limited to those conditions in which the microbes can be sustained. Thus, the conventional microbial process is incapable of optimizing the chemical conditions for growth of the particles in a manner that is independent of the conditions required for sustaining the microbes. For example, the conventional microbial process generally requires a completely aqueous medium, the use of metal ions and metal concentrations well below a lethal limit, and the use of non-toxic chemical components, all of which generally excludes the use of many of the additives and conditions that can be used in purely chemical processes for careful selection of particle size, shape, and crystalline form.

SUMMARY OF THE INVENTION

In one aspect, the invention is directed to a microbially-mediated method (herein also referred to as "complementary nanofermentation" or "complementary NF") for the production of nanoparticles having a metal chalcogenide (metal sulfide or metal selenide) composition. The microbially-mediated method described herein significantly departs from the conventional method in that the method described herein avoids contact of the microbes with the solution containing the metal ions. Thus, the microbes are not in contact with the metal ions or the resulting metal chalcogenide nanoparticles. The method achieves this by initiating production of a hydrogen chalcogenide-containing vapor (e.g., $H_2S$— or $H_2Se$-containing vapor) from a first solution containing chalcogen-reducing microbes (i.e., sulfur- or selenium-reducing microbes) and at least one reducible chalcogen-containing compound (i.e., chalcogen-containing source, which can be a reducible sulfur-containing or selenium-containing source) that can be converted to a hydrogen chalcogenide vapor by the chalcogen-reducing microbes, and directing the hydrogen chalcogenide-containing vapor to a second solution containing a metal salt dissolved in a solvent to produce metal chalcogenide nanoparticles in the second solution. In the process, the first and second solutions are separate; only the hydrogen chalcogenide-containing vapor produced from the first solution is transferred into the second solution.

More specifically, the method includes: (i) producing hydrogen chalcogenide-containing vapor from a microbial source, wherein said microbial source comprises: (a) chalcogen-reducing microbes capable of producing hydrogen chalcogenide vapor from a chalcogen-containing source; (b) a culture medium suitable for sustaining the chalcogen-reducing microbes; (c) at least one chalcogen-containing compound that can be converted to hydrogen chalcogenide vapor by the chalcogen-reducing microbes; and (d) at least one nutritive compound that provides donatable electrons to the chalcogen-reducing microbes during consumption of the nutritive compound by the chalcogen-reducing microbes; and (ii) directing the hydrogen chalcogenide-containing vapor into a metal-containing solution containing a metal salt dissolved in a solvent to produce metal chalcogenide nanoparticles in the metal-containing solution.

By virtue of the separate containment of the microbes from the metal-containing solution, several of the shortcomings of the conventional microbial process are overcome. For example, by the described process, the chemical and physical conditions used in producing the metal chalcogenide nanoparticles in the metal-containing solution are no longer restricted to only those conditions in which the microbes can be sustained. Instead, by the described process, the metal-containing solution can be subjected to any of the harsh chemical and physical conditions for growth of metal chalcogenide particles that would ordinarily result in death of the microbes. For example, by the described process, any metal ion species, including those known to be toxic to most organisms (e.g., Pb, Cd, or Hg) can be used. Moreover, the metal ions can be used in much higher concentrations than the lethal limit to microbes, and the metal-containing solution can also include any of a variety of chemicals that would ordinarily be toxic to microbes. Conversely, the microbial-containing solution can independently employ any of the conditions optimal for the microbial production of hydrogen sulfide or hydrogen selenide vapor, even if such conditions are adverse to the production of metal sulfide or metal selenide nanoparticles in the conventional process. The separate containment of the microbes from the metal-containing solution also advantageously avoids contamination of the resulting nanoparticles with microbial or culture matter, thereby eliminating the need for special separation and washing steps for this purpose.

Notably, the presently described process also provides several advantages over the bulk hydrogen sulfide processes of the art. As discussed above, in the bulk hydrogen sulfide process, metal ions are contacted with hydrogen sulfide to precipitate metal sulfide particles. Although the bulk hydrogen sulfide process produces metal sulfide particles, it has herein been surprisingly found that replacement of commercial (i.e., pure chemically-manufactured) hydrogen sulfide with microbially-produced hydrogen sulfide for producing metal sulfide particles results in a significant reduction in particle size, particularly nanoparticles in the lower nanoscale size range, e.g., below 100 nm. As further discussed in later parts of this application, it is believed that the presently described process achieves this advantage in particle size by virtue of the presence of size-controlling species (i.e., in addition to hydrogen sulfide) in the hydrogen sulfide-containing vapor produced by the microbes. The additional species are believed to be microbial metabolic byproducts. The additional species (e.g., carboxylate-containing species) are believed to function as size control agents during particle initiation and growth. An additional advantage of the presently described process is that it avoids the significant amount of hydrogen sulfide waste that generally occurs in the bulk hydrogen sulfide process.

The method described herein can furthermore produce a variety of metal chalcogenide (semiconductor) nanoparticle compositions on a commercially viable scale. In addition, the method can advantageously produce semiconductor nanoparticles of a particular particle size, morphology, electronic or photonic characteristic, dopant composition, or doping level. The nanoparticles produced herein possess any one or more of a diverse set of properties that make them useful. Some of the properties particularly considered herein include photovoltaic, photoluminescent, light-emitting, and thermoelectric properties. Such properties make these nanoparticles useful in one or more end applications, e.g., in photovoltaic, light-emitting, and thermoelectric materials and devices.

DETAILED DESCRIPTION OF THE INVENTION

The instant disclosure is directed to a method for producing metal chalcogenide nanoparticles. In the method, a hydrogen chalcogenide-containing vapor (i.e., $H_2S$— or $H_2Se$-containing vapor) is first produced from a microbial source, which includes sulfur-reducing or selenium-reducing microbes and a reducible chalcogen-containing source (i.e., one or more reducible sulfur-containing or selenium-containing compounds that can be converted to hydrogen sulfide or hydrogen selenide, respectively, by the sulfur-reducing or selenium-reducing microbes, respectively) in a culture medium. The hydrogen chalcogenide-containing vapor generally contains one or more size-controlling organic species (e.g., one or more carboxylic acid species, particularly acetic acid) in vapor form, in addition to the hydrogen chalcogenide. These size-controlling species are believed to be microbial metabolic byproducts produced in situ by the microbes. The hydrogen chalcogenide-containing vapor is then directed into a metal-containing solution to produce a sulfide or selenide of the metal in nanoparticle form. As the additional size-controlling species in the hydrogen chalcogenide-containing vapor have been unexpectedly found to be beneficial in producing smaller sized nanoparticles, it has been found to be preferable, for purposes of the invention, to feed the crude hydrogen chalcogenide-containing vapor directly into the metal-containing solution without a pretreatment (e.g., cleaning or purification) process on the vapor before the vapor contacts the metal-containing solution.

The microbial source from which the $H_2S$— or $H_2Se$-containing vapor is produced includes sulfur-reducing or selenium-reducing microbes in a culture medium suitable for sustaining the sulfur-reducing or selenium-reducing microbes. The chalcogen-reducing microbes considered herein are any microbes known in the art capable of producing $H_2S$ or $H_2Se$ from a source of chalcogen (source of sulfur or selenium, respectively). The microbe can be, for example, a eukaryotic or procaryotic (and either unicellular or multicellular) type of microbe having this ability. Of particular relevance herein are the procaryotic organisms, which are predominantly unicellular, and are divided into two domains: the bacteria and the archaea. The microbes can be, for example, thermophilic, mesophilic, psychrophilic, or psychrotolerant. The microbes can be, in addition, fermentative, metal-reducing, dissimilatory, sulfate-reducing, sulfite-reducing, elemental sulfur-reducing, organosulfur-reducing, or thiosulfate-reducing. The microbes may be those capable of directly reducing (i.e., in the absence of chemical means) a sulfur-containing or selenium-containing compound to $H_2S$ or $H_2Se$. In some embodiments, the microbes reduce the sulfur-containing or selenium-containing compound without intermediate production of elemental sulfur or elemental selenium. In other embodiments, the microbes reduce the sulfur-containing or selenium-containing compound with intermediate production of sulfur or selenium.

In one embodiment, the microbes considered herein are thermophilic, i.e., those organisms capable of thriving at temperatures of at least about 40° C. (and more typically, at least 45° C. or 50° C.) and up to about 100° C. or higher temperatures. Preferably, the thermophilic microbes are either bacteria or archaea, and particularly, those possessing an active hydrogenase system linked to high energy electron carriers.

A group of thermophilic bacteria particularly considered herein as sulfur-reducing microbes are the species within the genus *Thermoanaerobacter*. A particular species of *Thermoanaerobacter* considered herein is *Thermoanaerobacter* strain TOR-39, a sample of which was deposited with the American Type Culture Collection (10801 University Blvd., Manassas, Va. 20010) on Sep. 7, 2001 as accession number PTA-3695. Strain TOR-39 is a thermophile that grows optimally at temperatures from about 65 to 80° C. The conditions needed to grow and maintain this strain, including basal medium, nutrients, vitamins, and trace elements are detailed in U.S. Pat. No. 6,444,453, the entire contents of which are incorporated herein by reference. Some particular strains of *Thermoanaerobacter ethanolicus* particularly considered herein include *T. ethanolicus* strain C1 and *T. ethanolicus* strain M3.

Another group of thermophilic bacteria particularly considered herein as sulfur-reducing microbes are the species within the class Thermococci. An order of Thermococci particularly considered herein is Thermococcales. A family of Thermococcales particularly considered herein is Thermococcaceae. A genus of Thermococcaceae particularly considered herein is *Thermococcus*. A species of *Thermococcus* particularly considered herein is *Thermococcus litoralis*.

Another group of thermophilic bacteria particularly considered herein are the species within the genus *Thermoterrabacterium*. A species of *Thermoterrabacterium* particularly considered herein is *Thermoterrabacterium ferrireducens*, and particularly, strain JW/AS-Y7.

Still another group of thermophilic bacteria particularly considered herein are the species within the phylum Deinococcus-*Thermus*. A class of Deinococcus-*Thermus* particularly considered herein is Deinococci. An order of Deinococci particularly considered herein is Thermales. A genus of Thermales particularly considered herein is *Thermus*. A species of *Thermus* particularly considered herein is *Thermus* sp. strain SA-01.

Other thermophilic bacteria particularly considered herein include thermophilic species within any of the genera *Thermoanaerobacterium* (e.g., *T. thermosulfurigenes*, *T. polysaccharolyticum*, *T. zeae*, *T. aciditolerans*, and *T. aotearoense*), *Bacillus* (e.g., *B. infernus*), *Clostridium* (e.g., *C. thermocellum*), *Anaerocellum* (e.g., *A. thermophilum*), *Dictyoglomus* (e.g., *D. thermophilum*), and *Caldicellulosiruptor* (e.g., *C. acetigenus*, *C. hydrothermalis*, *C. kristjanssonii*, *C. kronotskiensis*, *C. lactoaceticus*, *C. owensensis*, and *C. saccharolyticus*).

In another embodiment, the microbes considered herein are mesophilic (e.g., organisms thriving at moderate temperatures of about 15-40° C.) or psychrophilic (e.g., organisms thriving at less than 15° C.). As used herein, the term "psychrophilic" also includes "psychrotolerant". Psychrophilic bacteria are typically found in deep marine sediments, sea ice, Antarctic lakes, and tundra permafrost. Some examples of such microbes include species within the genera *Shewanella* (e.g., *S. alga* strain PV-1, *S. alga*, PV-4, *S. pealeana*, W3-7-1, *S. gelidimarina*, and *S. frigidimarina*), *Clostridium* (e.g., *C. frigoris*, *C. lacusfryxellense*, *C. bowmanii*, *C. psychrophilum*, *C. laramiense*, *C. estertheticum*, and *C. schirmacherense*), *Bacillus* (e.g., *B. psychrosaccharolyticus*, *B. insolitus*, *B. globisporus*, *B. psychrophilus*, *B. cereus*, *B. subtilis*, *B. circulans*, *B. pumilus*, *B. macerans*, *B. sphaericus*, *B. badius*, *B. licheniformis*, *B. firmus*, *B. globisporus*, and *B. marinus*), and *Geobacter* (e.g., *G. sulfurreducens*, *G. bemidjiensis*, and *G. psychrophilus*). Of particular interest are those strains capable of anaerobic growth with nitrate as an electron acceptor. In some embodiments, the microbes are anaerobic.

In some embodiments, the microbes are one or more species selected from *Desulfovibrio* (e.g., *D. desulfuricans*, *D. gigas*, *D. salixigens*, and *D. vulgaris*), *Desulfolobus* (e.g., *D. sapovorans* and *D. propionicus*), *Desulfotomaculum* (e.g., *D. thermocisternum*, *D. thermobenzoicum*, *D. auripigmentum*, *D. nigrificans*, *D. orientis*, *D. acetoxidans*, *D. reducens*, and *D. ruminis*), *Desulfomicrobium* (e.g., *D. aestuarii*, *D. hypogeium*, and *D. salsuginis*), *Desulfomusa* (e.g., *D. hansenii*), *Thermodesulforhabdus* (e.g., *T. norvegica*) the order Desulfobacterales, and more particularly, the family Desulfobacteraceae, and more particularly, the genera *Desulfobacter* (e.g., *D. hydrogenophilus*, *D. postgatei*, *D. giganteus*, *D. halotolerans*, and *D. vibrioformis*), *Desulfobacterium* (e.g., *D. indolicum*, *D. anilini*, *D. autotrophicum*, *D. catecholicum*, *D. cetonicum*, *D. macestii*, *D. niacini*, *D. phenolicum*, *D. vacuolatum*), *Desulfobacula* (e.g., *D. toluolica* and *D. phenolica*), *Desulfobotulus* (*D. sapovorans* and *D. marinus*), *Desulfocella* (e.g., *D. halophila*), *Desulfococcus* (e.g., *D. multivorans* and *D. biacutus*), *Desulfofaba* (e.g., *D. gelida* and *D. fastidiosa*), *Desulfofrigus* (e.g., *D. oceanense* and *D. fragile*), *Desulfonema* (e.g., *D. limicola, D. ishimotonii*, and *D. magnum*), *Desulfosarcina* (e.g., *D. variabilis, D. cetonica,* and *D. ovata*), *Desulfospira* (e.g., *D. joergensenii*), *Desulfotalea* (e.g., *D. psychrophila* and *D. arctica*), and *Desulfotignum* (*D. balticum, D. phosphitoxidans*, and *D. toluenicum*). Several of the chalcogen-reducing microbes are either thermophilic or mesophilic. The chalcogen-reducing microbes may also be psychrophilic or psychrotolerant.

The chalcogen-reducing microbes can also be dissimilatory iron-reducing bacteria. Such bacteria are widely distributed and include some species in at least the following genera: *Bacillus, Deferribacter, Desulfuromonas, Desulfuromusa, Ferrimonas, Geobacter, Geospirillum, Geovibrio, Pelobacter, Sulfolobus, Thermoanaerobacter, Thermoanaerobium, Thermoterrabacterium*, and *Thermus*.

A few microbes are known to be have selenium-reducing abilities. Some of these microbes include, for example, *Bacillus selenitireducens, Veillonella atypica, Thauera selenatis, Sulfospirillum barnesii, Selenihalanerobacter shriftii, Pseudomonas stutzeri, Enterobacter hormaechei, Klebsiella pneumoniae*, and *Rhodobacter sphaeroides*. Reference is made to for example, M. J. Herbel et al., *Geomicrobiol. J.*, 20:587-602, 2003; J. S. Blum, *Arch. Microbial.*, 171: 19-30, 1998; and C. I. Pearce et al., *Environmental Technology*, 30:12, 1313-1326, November 2009.

It will also be appreciated that, in addition to the exemplary microorganisms listed above, other types of cultures, including mixed microbial cultures or uncharacterized microbial cultures from natural environments, and the like, may also be used in the invention. For example, cultures not yet characterized from natural hot springs where various metals are known to be present can demonstrate suitably high metal-reducing or selenium-reducing activity to carry out the inventive methods even though the exact species or genus of the microbes may be unknown and more than one species or genus may be present in said culture.

The choice of microbe generally involves trade-offs relating to cost, efficiency, and properties of the nanoparticle product. For example, thermophiles may be preferred when more product per unit of time is the primary consideration, since a high temperature process generally produces product at a faster rate. Conversely, psychrophilic or psychrotolerant microbes may be preferred in a case where one or more improved characteristics are of primary consideration, and where the improved characteristics are afforded to the product by virtue of the cooler process.

The microbes used in the method described herein can be obtained and cultured by any of the methods known in the art. Some of the general processes by which such bacteria may be used are taught in U.S. Pat. Nos. 6,444,453 and 7,060,473, the entire disclosures of which are incorporated herein by reference. The isolation, culturing, and characterization of thermophilic bacteria are described in, for example, T. L. Kieft et al., "Dissimilatory Reduction of Fe(III) and Other Electron Acceptors by a *Thermus* Isolate," *Appl. and Env. Microbiology*, 65 (3), pp. 1214-21 (1999). The isolation, culture, and characterization of several psychrophilic bacteria are described in, for example, J. P. Bowman et al., "*Shewanella gelidimarina* sp. nov. and *Shewanella frigidimarina* sp. nov., Novel Antarctic Species with the Ability to Produce Eicosapentaenoic Acid (20:5ω3) and Grow Anaerobically by Dissimilatory Fe(III) Reduction," *Int. J. of Systematic Bacteriology* 47 (4), pp. 1040-47 (1997). The isolation, culture, and characterization of mesophilic bacteria are described in, for example, D. R. Lovley et al., "*Geobacter metallireducens* gen. nov. sp. nov., a microorganism capable of coupling the complete oxidation of organic compounds to the reduction of iron and other metals," *Arch. Microbiol.*, 159, pp. 336-44 (1993), the disclosure of which is incorporated herein by reference in its entirety.

The culture medium for sustaining the microbes can be any of the known aqueous-based media known in the art useful for this purpose. The culture medium may also facilitate growth of the microbes. As is well known in the art, the culture medium includes such components as nutrients, trace elements, vitamins, and other organic and inorganic compounds, useful for the sustainment or growth of microbes.

In the method of the invention, the microbes are provided with at least one nutritive compound (electron donor). A nutritive compound is any compound or material capable of being oxidatively consumed by the microbes such that donatable electrons are provided to the microbes by the consumption process. The produced electrons are used by the microbes to reduce one or more sulfur-containing or selenium-containing compounds to $H_2S$ or $H_2Se$.

In one embodiment, the nutritive compound includes one or more carboxylate-containing compounds that can be oxidatively consumed by the microbes. Some examples of suitable carboxylate-containing compounds include salts of formate, acetate, propionate, butyrate, oxalate, malonate, succinate, fumarate, glutarate, lactate, pyruvate, glyoxylate, glycolate, and citrate.

In another embodiment, the nutritive compound includes one or more carbohydrates (i.e., saccharides, disaccharides, oligosaccharides, or polysaccharides) that can be oxidatively consumed by the microbes. Some examples of suitable carbohydrates include sugars, which are generally mono- and di-saccharides (e.g., glucose, fructose, sucrose, galactose, maltose, mannose, arabinose, xylose, and lactose), oligosaccharides, and polysaccharides (i.e., complex carbohydrates).

In another embodiment, the nutritive compound is or includes one or more inorganic species that can be oxidatively consumed by the microbes. The inorganic species can be, for example, an oxidizable gas, such as hydrogen or methane. Such gases can be oxidized by hydrogen-consuming or methane-consuming microbes which have the capacity to reduce a sulfur-containing or selenium-containing source to $H_2S$ or $H_2Se$ by the produced electrons.

In a first embodiment, the non-metal component includes a source of sulfur. The sulfur-containing compound being converted by the microbes to $H_2S$ should contain sulfur in a reducible state. Thus, the sulfur-containing compound should not be $H_2S$ itself or a sulfide ($S^{2-}$ or $HS^-$) salt. The source of sulfur (i.e., sulfur source) can be, for example, elemental sulfur)($S°$ or a sulfur-containing compound. In one instance, the sulfur-containing compound is an inorganic sulfur-containing compound. Some examples of inorganic sulfur-containing compounds include the inorganic sulfates (e.g., $Na_2SO_4$, $K_2SO_4$, $MgSO_4$, $(NH_4)_2SO_4$, $H_2SO_4$, or a metal sulfate), the inorganic sulfites (e.g., $Na_2SO_3$, $H_2SO_3$, or $(NH_4)_2SO_3$), inorganic thiosulfates (e.g., $Na_2S_2O_3$ or $(NH_4)_2S_2O_3$), sulfur dioxide, and peroxodisulfate (e.g., $Na_2S_2O_8$, $K_2S_2O_8$, or $(NH_4)_2S_2O_8$). In another instance, the sulfur-containing compound is an organosulfur compound. The organosulfur compound contains at least one hydrocarbon group and is typically characterized by the presence of at least one sulfur-carbon bond. Some examples of suitable organosulfur compounds include the hydrocarbon mercaptans or organothiols (e.g., methanethiol, ethanethiol, propanethiol, butanethiol, thiophenol, ethanedithiol, 1,3-propanedithiol, 1,4-butanedithiol, thiophene), the alcohol-containing mercaptans (e.g., 2-mercaptoethanol, 3-mercaptopropanol, 4-mercaptophenol, and dithiothreitol), the mercapto-amino acids (e.g., cysteine, homocysteine, methionine, thioserine, thiothreonine, and thiotyrosine), mercapto-peptides (e.g., glutathione), the mercapto-pyrimidines (e.g., 2-thiouracil, 6-methyl-2-thiouracil, 4-thiouracil, 2,4-dithiouracil, 2-thiocytosine, 5-methyl-2-thiocytosine, 5-fluoro-2-thiocytosine, 2-thiothymine, 4-thiothymine, 2,4-dithiothymine, and their nucleoside and nucleotide analogs), the mercapto-purines (e.g., 6-thioguanine, 8-thioadenine, 2-thioxanthine, 6-thioxanthine, 6-thiohypoxanthine, 6-thiopurine, and their nucleoside and nucleotide analogs), the thioethers (e.g., dimethylsulfide, diethylsulfide, diphenylsulfide, biotin), the disulfides (e.g., cystine, lipoic acid, diphenyl disulfide, iron disulfide, and 2-hydroxyethyldisulfide), the thiocarboxylic acids (e.g., thioacetic acid), the thioesters, the sulfonium salts (e.g., trimethylsulfonium or diphenylmethylsulfonium chloride), the sulfoxides (e.g., dimethylsulfoxide), the sulfones (e.g., dimethylsulfone), thioketones, thioamides, thiocyanates, isothiocyanates, thiocarbamates, dithiocarbamates, and trialkylphosphine sulfide (e.g., trioctylphosphine sulfide), thiourea compounds, or any of the inorganic sulfur-containing compounds, such as those enumerated above, which have been modified by inclusion of a hydrocarbon group. In particular embodiments, the organosulfur compound includes a sulfur-containing nucleic base (i.e., S-nucleobase), such as any of the mercapto-pyrimidines and mercapto-purines described above.

In a second embodiment, the non-metal component includes a selenium-containing compound. The selenium-containing compound being converted by the microbes to $H_2Se$ should contain selenium in a reducible state. Thus, the sulfur-containing compound should not be $H_2Se$ itself or a selenide ($Se^{2-}$ or $HSe^-$) salt. The source of selenium can be, for example, elemental selenium ($Se^0$) or a selenium-containing compound. In one instance, the selenium-containing compound is an inorganic selenium-containing compound. Some examples of inorganic selenium-containing compounds include the inorganic selenates (e.g., $Na_2SeO_4$, $K_2SeO_4$, $MgSeO_4$, $(NH_4)_2SeO_4$, $H_2SeO_4$, or a metal selenate), the inorganic selenites (e.g., $Na_2SeO_3$, $H_2SeO_3$, or $(NH_4)_2SeO_3$), inorganic selenosulfates (e.g., $Na_2SSeO_3$ or $(NH_4)_2SSeO_3$), selenium dioxide, and selenium disulfide. In another instance, the selenium-containing compound is an organoselenium compound. The organoselenium compound contains at least one hydrocarbon group and is typically characterized by the presence of at least one selenium-carbon bond. Some examples of suitable organoselenium compounds include the hydrocarbon selenols (e.g., methaneselenol, ethaneselenol, n-propaneselenol, isopropaneselenol, and selenophenol (benzeneselenol)), the seleno-amino acids (e.g., selenocysteine, selenocystine, selenohomocysteine, selenomethionine), the selenopyrimidines (e.g., 2-selenouracil, 6-methyl-2-selenouracil, 4-selenouracil, 2,4-diselenouracil, 2-selenocytosine, 5-methyl-2-selenocytosine, 5-fluoro-2-selenocytosine, 2-selenothymine, 4-selenothymine, 2,4-diselenothymine, and their nucleoside and nucleotide analogs), the selenopurines (e.g., 6-selenoguanine, 8-selenoadenine, 2-selenoxanthine, 6-selenoxanthine, 6-selenohypoxanthine, 6-selenopurine, and their nucleoside and nucleotide analogs), the selenides (e.g., dimethylselenide, diethylselenide, and methylphenylselenide), the diselenides (e.g., dimethyldiselenide, diethyldiselenide, and diphenyldiselenide), the selenocarboxylic acids (e.g., selenoacetic acid, selenopropionic acid), the selenosulfides (e.g., dimethylselenosulfide), the selenoxides (e.g., dimethylselenoxide and diphenylselenoxide), the selenones, the selenonium salts (e.g., dimethylethylselenonium chloride), the vinylic selenides, selenopyrylium salts, trialkylphosphine selenide (e.g., trioctylphosphine selenide, i.e., TOPSe), selenourea compounds, or any of the inorganic selenium-containing compounds, such as those enumerated above, which have been modified by inclusion of a hydrocarbon group. In particular embodiments, the organoselenium compound includes a selenium-containing nucleic base (i.e., Se-nucleobase), such as any of the selenopyrimidines and selenopurines described above.

The reaction components of the microbial source (i.e., chalcogen-reducing microbes, culture medium, chalcogen-containing source, and one or more nutritive compounds) are combined in a suitable container and subjected to conditions (e.g., temperature, pH, and either oxic or anoxic conditions) suitable for the microbes to produce $H_2S$ or $H_2Se$ vapor. The container for holding the microbial source generally includes at least one outlet attached to a conduit (e.g., a tube or pipe) for the $H_2S$-containing vapor or $H_2Se$-containing vapor to exit and be transported into the metal-containing solution. Generally, the outlet of the conduit is positioned below the surface of the metal-containing solution so that the $H_2S$-containing vapor or $H_2Se$-containing vapor bubbles into the metal-containing solution. The metal-containing solution, which is held in a separate compartment, is generally equipped with a mixer to facilitate mixing and intimate contact of the $H_2S$-containing vapor or $H_2Se$-containing vapor with the metal-containing solution.

When thermophilic microbes are used, the temperature at which the microbial source is maintained during production of $H_2S$ or $H_2Se$ is typically at least, for example, 40° C., 45° C., 50° C., 55° C., 60° C., 65° C., 70° C., 75° C., 80° C., 85° C., or 90° C. depending on the type of thermophilic microbes being used. Any range resulting from any two of the foregoing values is also contemplated herein. When mesophilic microbes are used, the temperature can preferably be at least 15° C., 20° C., 25° C., or 30° C., and up to any of the temperatures given above for thermophilic microbes. When psychrophilic microbes are used, the temperature at which the reaction is conducted can preferably be less than, for example, 40° C., or at or less than 35° C., 30° C., 25° C., 20° C., 15° C., 10° C., 5° C., 0° C., or −5° C., or any range resulting from any two of the foregoing values. It is to be appreciated that, even though different exemplary temperatures have been given for each type of microbe, each type of microbe may be capable of thriving in temperatures well outside the typical temperatures given above. For example, a thermophilic microbe may also be capable of thriving to a useful extent at temperatures below 40° C. where mesophilic microbes traditionally thrive; or mesophilic or thermophilic microbes may be capable of thriving to a useful extent at temperatures below 15° C. (i.e., by being psychrotolerant in addition to mesophilic or thermophilic). Particularly when employing *Thermoanaerobacter* sp. strain TOR-39, the temperature is preferably maintained between about 45° C. and 75° C.

The pH of the microbial source of $H_2S$ or $H_2Se$ can also be suitably adjusted. Generally, when using thermophilic bacteria, the pH value is preferably within the range of 6.5-9. For example, particularly when employing *Thermoanaerobacter* sp. strain TOR-39, the pH is preferably maintained at a level between about 6.9 and 7.5. In different embodiments, depending on the microbe and other conditions, the pH is preferably acidic by being less than 7 (e.g., a pH of or less than 6.5, 6.0, 5.5, 5.0, 4.5, 4.0, 3.5, 3.0, 2.5, 2.0, 1.5, 1.0, or a range resulting from any two of these values), or preferably alkaline by being above 7 (e.g., a pH of or greater than 7.5, 8.0, 8.5, 9.0, 9.5, 10, 10.5, 11, 11.5, ora range resulting from any two of these values), or preferably approximately neutral by having a pH of about 7, e.g., 6.5-7.5.

The metal-containing solution contains one or more types of metals in ionic form, particularly as described above. The one or more metals are typically in the form of a salt or coordination compound, wherein "compound" as used herein also includes a "material" or "polymer". The metal ions in the metal salt(s) may be selected from, for example, any one or more of the transition metals and main group metals. As well known, the transition metals generally refer to any of the elements in Groups 3-12 of the Periodic Table of the Elements (or a subset therein), while the main group metals generally refer to Groups 13-15 of the Periodic Table (or a subset therein). Some metals particularly considered herein include, for example, V, Cr, Mn, Fe, Co, Ni, Cu, Zn, Mo, W, Pd, Pt, Au, Ag, Cd, Hg, Ga, In, Tl, Ge, Sn, Pb, Sb, and Bi. In some embodiments, the metal ion in the metal salt may be selected from, for example, one or more metal ions selected from the group consisting of Zn, Cu, Sn, Cd, Fe, Ga, In, Pb, and Hg. The metal ions may be in any of their known oxidation states, e.g., $Fe^{+2}$ and $Fe^{+3}$. However, in some embodiments, the metal ion is in its lowest (yet stable) positive oxidation state, e.g., monovalent or divalent oxidation state, if applicable.

In the metal-containing solution, the metal salt is dissolved in a suitable solvent. Significantly, by virtue of the separation of microbes from metal salts in the presently described process, the presently described process can employ a solvent in the metal-containing solution that would ordinarily be harmful or deadly to microbes. This ability is in contrast to biofermentation processes of the art, which include the microbes in direct contact with the metal salts, thereby significantly limiting the choice of solvent to only aqueous-based, and typically, solely water. In one set of embodiments, the solvent in the metal-containing solution is aqueous-based, i.e., it includes water. The aqueous-based solvent may be solely water, or water admixed with a water-soluble organic solvent, e.g., an alcohol, acetone, acetonitrile, DMF, or DMSO. In other embodiments, the solvent in the metal-containing solution is or includes at least one organic solvent. The organic solvent may be protic (e.g., an alcohol, such as methanol, ethanol, or isopropanol) or non-protic, wherein the non-protic solvent may be substantially polar (e.g., acetone, DMF, DMSO, or acetonitrile) or moderately or substantially non-polar (e.g., methylene chloride, chloroform, tetrahydrofuran, diethyl ether, benzene, or toluene).

Some examples of metal salts include the metal halides (e.g., $CuCl_2$, $CdCl_2$, $ZnCl_2$, $ZnBr_2$, $GaCl_3$, $InCl_3$, $FeCl_2$, $FeCl_3$, $PbCl_2$, $HgCl_2$, $SnCl_2$, and $SnCl_4$), metal nitrates (e.g., $Cd(NO_3)_2$, $Ga(NO_3)_3$, $In(NO_3)_3$, and $Fe(NO_3)_3$), metal perchlorates, metal carbonates (e.g., $CdCO_3$), metal sulfates (e.g., $CdSO_4$, $FeSO_4$, and $ZnSO_4$), metal oxides (e.g., $Fe_2O_3$, CdO, $Ga_2O_3$, $In_2O_3$, ZnO, SnO, $SnO_2$), metal hydroxides (e.g., $Fe(OH)_3$ and $Zn(OH)_2$), metal oxyhydroxides (e.g., FeOOH, or FeO(OH), and their alternate forms), metal-EDTA complexes, metal amines (e.g., metal alkylamine, piperidine, pyridine, or bipyridine salt complexes), metal carboxylates (e.g., zinc acetate or cadmium acetate), and metal acetylacetonates (i.e., metal-acac) complexes.

One or more dopant species can be included in the metal-containing solution in order to likewise dope the resulting metal sulfide nanoparticles. The dopant can be any metal or non-metal species, such as any of the metal and non-metal species described above. In some embodiments, the dopant may be or include one or more transition metal or lanthanide elements. Generally, the dopant is present in an amount of less than 0.5 molar percent of the resulting nanoparticles, or in different embodiments, less than or up to 0.4, 0.3, 0.2, 0.1, 0.05, 0.02, or 0.01 molar percent of the resulting nanoparticles. Some examples of doped compositions include ZnS:Ni, wherein Ni functions as a dopant, as described in, for example, Bang et al., *Advanced Materials*, 20:2599-2603 (2008), $Zn_xCd_{1-x}S$ doped compositions, as described in Wang et al., *Journal of Physical Chemistry C* 112:16754-16758 (2008), and ZnS:Mn and ZnS:Cu compositions, as described in Song et al., *Journal of Physics and Chemistry of Solids*, 69:153-160 (2008). In other embodiments, a dopant is excluded, or alternatively, one or more of any of the generic or specific dopants described above are excluded.

As the metal-containing solution is separate from the microbes according to the described process, unlike biofermentation processes of the art, the total metal concentration in the metal-containing solution does not need to be below a concentration at which the metals are toxic to the microbes. Thus, the total metal concentration in the metal-containing solution can be any suitable metal concentration for producing metal sulfide nanoparticles. In some embodiments, the metal concentration is at least or above 100 mM, 200 mM, 500 mM, 1 M, 2 M, or 5 M.

In one set of embodiments, the metal-containing solution (i.e., the metal salt therein) contains a single species of metal ion, which results in metal chalcogenide nanoparticles having a mono-metal sulfide or mono-metal selenide composition. The single metal in the metal-containing solution and resulting mono-metal chalcogenide composition may be selected from any of the transition metals or main group metals provided earlier above. In more specific embodiments, the single metal in the metal-containing solution and resulting mono-metal sulfide or selenide composition is Zn, Cu, Sn, Cd, Fe, Ga, In, Pb, or Hg. The metal chalcogenide can be, for example, ZnX, CuX, $Cu_2X$, SnX, $SnX_2$, CdX, FeX, $Fe_2X_3$, $Ga_2X_3$, $In_2X_3$, PbX, and HgX, wherein X is S or Se or a combination thereof. Some examples of mono-metal sulfide compositions include, for example, ZnS, CuS, $Cu_2S$, SnS, $SnS_2$, CdS, FeS, $Fe_2S_3$, $Ga_2S_3$, $In_2S_3$, PbS, and HgS. Some examples of mono-metal selenide compositions include, for example, ZnSe, CuSe, $Cu_2Se$, SnSe, $SnSe_2$, CdSe, FeSe, $Fe_2Se_3$, $Ga_2Se_3$, $In_2Se_3$, PbSe, and HgSe. Some examples of mono-metal sulfide-selenide compositions include, for example, $ZnS_{0.5}Se_{0.5}$ and $CdS_{0.5}Se_{0.5}$.

In a second set of embodiments, the metal-containing solution (i.e., the metal salt(s) therein) contains at least two species of metal ions, which results in metal chalcogenide nanoparticles having a multi-metal (e.g., bi-metal, tri-metal, or higher-metal) sulfide or multi-metal selenide composition. The at least two metals in the metal-containing solution and resulting multi-metal chalcogenide composition may be selected from any of the transition metals or main group metals provided earlier above. In more specific embodiments, the metal salt(s) contains at least two species of metal ions selected from Zn, Cu, Sn, Cd, Fe, Ga, In, Pb, and Hg, which results in metal sulfide or metal selenide nanoparticles having a multi-metal sulfide or selenide composition containing at least two of the foregoing species of metal ions. The metal chalcogenide can be, for example, $Zn_xCd_{1-x}X$, $Zn_xCu_{1-x}X$, $Zn_xSn_{1-x}X$, $Zn_xFe_{1-x}X$, $Ga_xIn_{2-x}X_3$, $Cd_xCu_{1-x}X$, $Cd_xSn_{1-x}X$, $Cd_xFe_{1-x}X$, $Cu_xSn_{1-x}X$, or $Cu_xFe_{1-x}X$, wherein x is an integral or non-integral numerical value greater than 0 and less than 1 in the expression "1–x" (or greater than 0 and less than 2 for the expression "2–x"), and wherein X is S or Se or a combination thereof. Some examples of multi-metal sulfide compositions include, for example, $Zn_xCd_{1-x}S$, $Zn_xCu_{1-x}S$, $Zn_xSn_{1-x}S$, $Zn_xFe_{1-x}S$, $Ga_xIn_{2-x}S_3$, $Cd_xCu_{1-x}S$, $Cd_xSn_{1-x}S$, $Cd_xFe_{1-x}S$, $Cu_xSn_{1-x}S$, and $Cu_xFe_{1-x}S$. Some examples of multi-metal selenide compositions include, for example, $Zn_xCd_{1-x}Se$, $Zn_xCu_{1-x}Se$, $Zn_xSn_{1-x}Se$, $Zn_xFe_{1-x}Se$, $Ga_xIn_{2-x}Se_3$, $Cd_xCu_{1-x}Se$, $Cd_xSn_{1-x}Se$, $Cd_xFe_{1-x}Se$, $Cu_xSn_{1-x}Se$, and $Cu_xFe_{1-x}Se$. Some examples of multi-metal sulfide-selenide compositions include, for example, $Zn_xCd_{1-x}S_{0.5}Se_{0.5}$, $Zn_xCu_{1-x}S_{0.5}Se_{0.5}$, $Zn_xSn_{1-x}S_{0.5}Se_{0.5}$, $Zn_xFe_{1-x}S_{0.5}Se_{0.5}$, $Ga_xIn_{2-x}S_2Se$, $Cd_xCu_{1-x}S_{0.5}Se_{0.5}$, $Cd_xSn_{1-x}S_{0.5}Se_{0.5}$, $Cd_xFe_{1-x}S_{0.5}Se_{0.5}$, $Cu_xSn_{1-x}S_{0.5}Se_{0.5}$, and $Cu_xFe_{1-x}S_{0.5}Se_{0.5}$. Any of the multi-metal sulfide or selenide compositions may also include arsenic, antimony, or bismuth as a ternary or quaternary metal.

When two or more metals are included in the metal-containing solution, the molar ratio of metal ions can be adjusted such that a particular molar ratio of metals is provided in the nanoparticle product. Typically, the molar ratio of metal ions in the metal-containing solution is the molar ratio of metals found in the nanoparticle product. However, the molar ratio of metals in the product may, in several embodiments, differ from the molar ratio of metals in the metal-containing solution. In a particular embodiment, a desired molar ratio of metals is achieved in the nanoparticle product by suitable adjustment of metal ratios in the metal-containing solution.

In one set of embodiments, the metal chalcogenide nanoparticles have a multi-metal composition that is a CIGS-type composition according to the following formula:

$$Cu(In_xGa_{1-x})X_2 \tag{1}$$

In Formula (1) above, x is an integral or non-integral numerical value of or greater than 0 and less than or equal to 1, and X represents S, Se, or a combination thereof. One or more additional metals, such as any of the metals provided above, may or may not be included in a doping or stoichiometric amount in Formula (1). Compositions according to formula (1) and subformulas containing one or more additional metals are collectively referred to herein as CIGS compositions. The CIGS compositions encompassed by Formula (1) may also contain a relative molar ratio of Cu that diverges from 1. Some examples of sulfide compositions according to Formula (1) include $CuInS_2$, $CuIn_{0.9}Ga_{0.1}S_2$, $CuIn_{0.8}Ga_{0.2}S_2$, $CuIn_{0.7}Ga_{0.3}S_2$, $CuIn_{0.6}Ga_{0.4}S_2$, $CuIn_{0.5}Ga_{0.5}S_2$, $CuIn_{0.4}Ga_{0.6}S_2$, $CuIn_{0.3}Ga_{0.7}S_2$, $CuIn_{0.2}Ga_{0.8}S_2$, $CuIn_{0.1}Ga_{0.9}S_2$, and $CuGaS_2$. Some examples of selenide compositions according to Formula (1) include $CuInSe_2$, $CuIn_{0.9}Ga_{0.1}Se_2$, $CuIn_{0.8}Ga_{0.2}Se_2$, $CuIn_{0.7}Ga_{0.3}Se_2$, $CuIn_{0.6}Ga_{0.4}Se_2$, $CuIn_{0.5}Ga_{0.5}Se_2$, $CuIn_{0.4}Ga_{0.6}Se_2$, $CuIn_{0.3}Ga_{0.7}Se_2$, $CuIn_{0.2}Ga_{0.8}Se_2$, $CuIn_{0.1}Ga_{0.9}Se_2$, and $CuGaSe_2$. Some examples of sulfide-selenide compositions according to Formula (1) include $CuInSSe$, $CuIn_{0.9}Ga_{0.1}SSe$, $CuIn_{0.8}Ga_{0.2}SSe$, $CuIn_{0.7}Ga_{0.3}SSe$, $CuIn_{0.6}Ga_{0.4}SSe$, $CuIn_{0.5}Ga_{0.5}SSe$, $CuIn_{0.4}Ga_{0.6}SSe$, $CuIn_{0.3}Ga_{0.7}SSe$, $CuIn_{0.2}Ga_{0.8}SSe$, $CuIn_{0.1}Ga_{0.9}SSe$, and $CuGaSSe$. To prepare any of the above CIGS composition, the metal-containing solution should contain at least Cu, In, and Ga ions (as metal salts). If additional metals are to be included in Formula (1), metal salts of such metals should also be included in the metal-containing solution.

In another set of embodiments, the metal chalcogenide nanoparticles have a multi-metal composition that is a kesterite-type composition according to the following formula:

$$M_3SnX_4 \tag{2}$$

In Formula (2), M represents at least one metal (typically divalent) other than Sn, and X represents S, Se, or a combination thereof. M can be, for example, one, two, three, or four metals selected from V, Cr, Mn, Co, Ni, Fe, Zn, Cd, Cu, Mo, W, Pd, Pt, Au, Ag, Hg, Ga, In, Tl, Ge, Pb, Sb, and Bi. In particular embodiments, M represents one, two, three, or four metals selected from Cu, Fe, Zn, and Cd. The relative molar ratio of Sn encompassed by Formula (2) may diverge from 1. To prepare any of the above kesterite-type compositions, the metal-containing solution should contain the one or more metals represented by M along with Sn (as metal salts). If additional metals are to be included in Formula (2), metal salts of such metals should also be included in the metal-containing solution.

In some embodiments, the kesterite-type composition of Formula (2) is according to the following sub-generic formula:

$$Cu_{3-y}M'_ySnX_4 \tag{2a}$$

In Formula (2a), M' represents one or more metals other than Cu or Sn. In particular embodiments, M' represents one, two, or three metals selected from, for example, V, Cr, Mn, Co, Ni, Fe, Zn, Cd, Mo, W, Pd, Pt, Au, Ag, Hg, Ga, In, Tl, Ge, Pb, Sb, and Bi. Some metals particularly considered herein include Fe, Zn, and Cd. The subscript y is an integral or non-integral numerical value of or greater than 0 and up to or less than 1, 2, or 3. In different embodiments, y can be selected to be a value of precisely or about 1, 2, or 3, or a non-integral value between 0 and 3, wherein the term "about" generally indicates within ±0.5, ±0.4, ±0.3, ±0.2, or ±0.1 of the value. For example, a value of about 1 generically indicates, in its broadest sense, that x can be 0.5 to 1.5 (i.e., 1±0.5).

Some particular kesterite-type compositions of Formula (2a) are encompassed by the following sub-generic formula:

$$Cu_{3-y}Zn_ySnX_4 \tag{2a-1}$$

In Formula (2a-1), y is as described above under Formula (2a). Some examples of sulfide compositions according to Formula (2a-1) include $Cu_3SnS_4$ (kuramite), $Cu_2ZnSnS_4$ (kesterite), $CuZn_2SnS_4$, $Cu_{0.5}Zn_{2.5}SnS_4$, $Cu_{2.5}Zn_{0.5}SnS_4$, $Cu_{1.5}Zn_{1.5}SnS_4$, and $Zn_3SnS_4$. Some examples of selenide compositions according to Formula (2a-1) include $Cu_3SnSe_4$, $Cu_2ZnSnSe_4$, $CuZn_2SnSe_4$, $Cu_{0.5}Zn_{2.5}SnSe_4$, $Cu_{2.5}Zn_{0.5}SnSe_4$, $Cu_{1.5}Zn_{1.5}SnSe_4$, and $Zn_3SnSe_4$.

Other particular kesterite-type compositions of Formula (2a) are encompassed by the following sub-generic formula:

$$Cu_{3-y}Fe_ySnX_4 \tag{2a-2}$$

In Formula (2a-2), y is as described above under Formula (2a). Some examples of sulfide compositions according to Formula (2a-2) include $Cu_3SnS_4$, $Cu_2FeSnS_4$ (stannite), $CuFe_2SnS_4$, $Cu_{0.5}Fe_{2.5}SnS_4$, $Cu_{2.5}Fe_{0.5}SnS_4$, $Cu_{1.5}Fe_{1.5}SnS_4$, and $Fe_3SnS_4$. Some examples of selenide compositions according to Formula (2a-2) include $Cu_3SnSe_4$, $Cu_2FeSnSe_4$, $CuFe_2SnSe_4$, $Cu_{0.5}Fe_{2.5}SnSe_4$, $Cu_{2.5}Fe_{0.5}SnSe_4$, $Cu_{1.5}Fe_{1.5}SnSe_4$, and $Fe_3SnSe_4$.

Other particular kesterite-type compositions of Formula (2a) are encompassed by the following sub-generic formula:

$$Cu_{3-y}Cd_ySnX_4 \tag{2a-3}$$

In Formula (2a-3), y is as described above under Formula (2a). Some examples of sulfide compositions according to Formula (2a-3) include $Cu_3SnS_4$, $Cu_2CdSnS_4$ (cernyite), $CuCd_2SnS_4$, $Cu_{0.5}Cd_{2.5}SnS_4$, $Cu_{2.5}Cd_{0.5}SnS_4$, $Cu_{1.5}Cd_{1.5}SnS_4$, and $Cd_3SnS_4$. Some examples of selenide compositions according to Formula (2a-3) include $Cu_3SnSe_4$, $Cu_2CdSnSe_4$, $CuCd_2SnSe_4$, $Cu_{0.5}Cd_{2.5}SnSe_4$, $Cu_{2.5}Cd_{0.5}SnSe_4$, $Cu_{1.5}Cd_{1.5}SnSe_4$, and $Cd_3SnSe_4$.

In other embodiments, the kesterite-type composition of Formula (2) is encompassed by the following sub-generic formula:

$$Cu_2M'_zM'_{1-z}SnX_4 \quad (2b)$$

In Formula (2b), each M' is independently defined as above under Formula (2a), z is an integral or non-integral numerical value of or greater than 0 and up to or less than 1, and X represents S, Se, or a combination thereof. In particular embodiments, the two M' metals in Formula (2b) are not the same, i.e., the two M' metals in Formula (2b) are different. The relative molar ratio of Sn encompassed by Formula (2b) may diverge from 1, and the relative molar ratio of Cu encompassed by Formula (2b) may diverge from 2.

Some particular kesterite-type compositions of Formula (2b) are encompassed by the following sub-generic formula:

$$Cu_2Fe_zZn_{1-z}SnX_4 \quad (2b\text{-}1)$$

Some examples of sulfide compositions according to Formula (2b-1) include $Cu_2Fe_{0.1}Zn_{0.9}SnS_4$, $Cu_2Fe_{0.2}Zn_{0.8}SnS_4$, $Cu_2Fe_{0.3}Zn_{0.7}SnS_4$, $Cu_2Fe_{0.4}Zn_{0.6}SnS_4$, $Cu_2Fe_{0.5}Zn_{0.5}SnS_4$, $Cu_2Fe_{0.6}Zn_{0.4}SnS_4$, $Cu_2Fe_{0.7}Zn_{0.3}SnS_4$, $Cu_2Fe_{0.8}Zn_{0.2}SnS_4$, and $Cu_2Fe_{0.9}Zn_{0.1}SnS_4$. Some examples of selenide compositions according to Formula (2b-1) include $Cu_2Fe_{0.1}Zn_{0.9}SnSe_4$, $Cu_2Fe_{0.2}Zn_{0.8}SnSe_4$, $Cu_2Fe_{0.3}Zn_{0.7}SnSe_4$, $Cu_2Fe_{0.4}Zn_{0.6}SnSe_4$, $Cu_2Fe_{0.5}Zn_{0.5}SnSe_4$, $Cu_2Fe_{0.6}Zn_{04}SnSe_4$, $Cu_2Fe_{0.7}Zn_{0.3}SnSe_4$, $Cu_2Fe_{0.8}Zn_{02}SnSe_4$, and $Cu_2Fe_{0.9}Zn_{01}SnSe_4$. The relative molar ratio of Sn encompassed by formula (2b-1) may diverge from 1, and the relative molar ratio of Cu encompassed by formula (2b-1) may diverge from 2.

In other embodiments, the kesterite-type compositions of Formula (2) are encompassed by the following sub-generic formula:

$$CuM'_vM'_{2-v}SnX_4 \quad (2c)$$

In Formula (2c), each M' is defined as above under formula (2a), v is an integral or non-integral numerical value of at least or greater than 0 and up to or less than 1 or 2, and X represents S, Se, or a combination thereof. In particular embodiments, the two M' metals in Formula (2c) are not the same, i.e., the two M' metals in Formula (2c) are different. In different embodiments, v can be selected to be a value of precisely or about 1 or 2, or a non-integral value between 0 and 2, wherein the term "about" is as defined under Formula (2a). The relative molar ratio of Sn and Cu encompassed by formula (2c) may each diverge from 1.

Some particular kesterite-type compositions of Formula (2c) are encompassed by the following sub-generic formula:

$$CuFe_vZn_{2-v}SnX_4 \quad (2c\text{-}1)$$

Some examples of sulfide compositions according to Formula (2c-1) include $CuFe_{0.5}Zn_{1.5}SnS_4$, $CuFeZnSnS_4$, and $CuFe_{1.5}Zn_{0.5}SnS_4$. The relative molar ratio of Sn and Cu encompassed by formula (2c-1) may each diverge from 1. Some examples of selenide compositions according to Formula (2c-1) include $CuFe_{0.5}Zn_{1.5}SnSe_4$, $CuFeZnSnSe_4$, and $CuFe_{1.5}Zn_{0.5}SnSe_4$. The relative molar ratio of Sn and Cu encompassed by formula (2c-1) may each diverge from 1.

In the method for producing metal sulfide nanoparticles, the metal-containing solution is contacted with the $H_2S$-containing or $H_2Se$-containing vapor emanating from the microbial source, typically by bubbling the $H_2S$-containing or $H_2Se$-containing vapor through the metal-containing solution, with optional mixing of the metal-containing solution. During contact of the metal-containing solution with the $H_2S$-containing or $H_2Se$-containing vapor, the metal-containing solution may be maintained under an oxygen-containing (i.e., oxic) or substantially oxygen-deficient (i.e., substantially or completely anoxic) atmosphere. If anoxic conditions are used, the atmosphere over the metal-containing solution may be composed of any gas or gas mixture not containing oxygen, and typically one or more inert gases, e.g., nitrogen or a noble gas, such as argon. In some embodiments, the inert gas enters the metal-containing solution as a component of the vapor from the microbial source, i.e., in embodiments where an inert gas is sparged into the microbial source where $H_2S$ or $H_2Se$ is being produced.

The method is practiced by contacting the metal-containing solution with the $H_2S$-containing or $H_2Se$-containing vapor under conditions that facilitate or induce the formation of metal sulfide or metal selenide nanoparticles therein, respectively. Some of the conditions that can affect formation of metal sulfide or metal selenide nanoparticles from the metal-containing solution include temperature, metal concentration, pH, flow rate of $H_2S$-containing or $H_2Se$-containing vapor, and the presence or absence of stabilizing (e.g., size-controlling) agents or surfactants. In some embodiments, the reaction conditions may not require any special measures other than bubbling the $H_2S$-containing or $H_2Se$-containing vapor into the metal-containing solution, with optional mixing, at room temperature (e.g., 15-25° C.) and waiting for nanoparticles to grow over a period of time. In other embodiments, the combined reaction components are, for example, heated, cooled, modified in pH, or reacted with stabilizing agents or surfactants in order to facilitate, induce, or otherwise modify nanoparticle formation and/or growth. Any of the temperatures and pHs provided above for the microbial source may independently be employed in the metal-containing solution. Depending on the conditions used, the time until nanoparticle development may be a few minutes or within an hour (e.g., 1-60 minutes) or several hours, or days or weeks (e.g., 1-7 days, or 1-3 weeks). Generally, nanoparticles produced over a shorter time period tend to be smaller than nanoparticles produced over a longer time period under otherwise identical conditions. Nevertheless, by virtue of the natural size-controlling agents produced by the microbes, the described process has the ability to produce nanoparticles of a particular size in substantial independence of the flow rate of the $H_2S$-containing or $H_2Se$-containing vapor and its reaction time with the metal-containing salt. In other words, by the described process, a stable size equilibrium may be reached during growth, which is not disturbed much by the flow rate of the $H_2S$-containing or $H_2Se$-containing vapor and its reaction time with the metal-containing salt. However, other factors, e.g., temperature, metal concentration, pH, and presence of surface-active agents (e.g., capping agents or surfactants) can shift this equilibrium and provide a way to adjust the size of the nanoparticles. The method of the invention can be performed in a batchwise manner or in a continuous manner.

In addition to selecting reaction conditions (e.g., temperature, reaction time, and pH) on the basis of permitting or inducing the formation of nanoparticles, the reaction conditions can also be selected for numerous other purposes, including to modify or optimize the product yield, production efficiency, particle size, particle composition or phase (e.g., crystalline vs. semi-crystalline vs. amorphous), or particle morphology. For example, lower reaction temperatures may be employed to provide a more pure or single-crystalline product.

Once the nanoparticles are produced, they are isolated (i.e., separated) from the reaction components and byproducts formed by the reaction products. Any method known in the art for separation of nanoparticles from reaction components can be used herein.

In one embodiment, nanoparticles are separated from the reaction components by allowing the nanoparticles to settle to the bottom of the container and then decanting the liquid medium or filtering off the nanoparticle product. This settling may be accomplished with or without centrifugation. When centrifugation is used, the centrifugal (i.e., "g" force) causes settling of denser nanoparticles to the bottom or distal end of the spun containers. The collected nanoparticle product may be washed one or more times to further purify the product. The reaction container may optionally be fitted with a drain valve to allow the solid product to be removed without decanting the medium or breaking gas seals.

In another embodiment, the container in which the reaction components is housed is attached to (or includes) an external trap from which the nanoparticle product can be removed. The trap is preferably in the form of a recess situated below flowing reaction solution. Nanoparticles in the flowing reaction solution are denser than the reaction solution, and hence, will settle down into the trap. The flowing reaction solution is preferably recirculated.

In another embodiment, a filter is used to trap the nanoparticles. The filter can be in the form of multiple filters that trap successively smaller particles. Depending on the particle size and other variables, one or more filters that trap the nanoparticles may contain a pore size of no more than about 0.5, 0.4, 0.3, 0.25, 0.2, 0.1, or 0.05 µm.

In yet another embodiment, in a case where the nanoparticle product is magnetic, a magnetic source (e.g., electromagnet or other suitable magnetic field-producing device) can be employed to collect the nanoparticles. The magnetic source can be used as the sole means of separation, or used in combination with other separation means, such as a trap or filter.

In some embodiments, one or more stabilizing (i.e., surface-active or size-controlling) compounds or materials are included in the metal-containing solution for stabilizing or controlling the size of the produced nanoparticles during growth. The stabilizing agent is typically a soft-binding ligand that includes either sulfur or phosphorus, such as, for example, glutathione, 2-mercaptoethanol, triphenylphosphine, thioglycerol, long-chain thiol, metal-binding polymer, or other surface-active substance. In another embodiment, stabilizing compounds are excluded in the method, whereby the produced metal sulfide or metal selenide nanoparticles are sufficiently stable in the absence of a stabilizing compound or material, except for those naturally provided by the microbes as breakdown products of nutritive compounds.

The semiconductor nanoparticles have a size (i.e., "diameter" for spherical or polyhedral nanoparticles) in the nanoscale regime, i.e., less than 1 micron (1 µm). The term "size" can be further specified as the "average crystallite size" (ACS), which refers to individual crystallites within an agglomeration of crystallites or as dispersed with no agglomeration. Typically, individual crystallites will agglomerate to some extent. Thus, the term "size" can alternatively refer to the diameter of the agglomerates, also known as the "effective diameter" or "secondary particle size". It has herein been surprisingly found that, although the average crystallite size of nanoparticles produced by the above-described method is similar to the crystallite size of nanoparticles produced by the conventional biofermentation process, the effective diameter of nanoparticles produced by the above-described method is generally much smaller. In particular, while it has generally been found that the effective diameter of nanoparticles produced by the conventional biofermentation process is well into the micron size (e.g., at least 10, 20, or 30 microns), the effective diameter of nanoparticles produced by the method described herein is generally in the nanoscale, i.e., below 1 micron, 500 nm, 200 nm, 100 nm, or 50 nm. In different embodiments, the nanoparticles produced herein have an effective diameter of about 1 nm, 2 nm, 3 nm, 4 nm, 5 nm, 10 nm, 12 nm, 15 nm, 20 nm, 25 nm, 30 nm, 40 nm, 50 nm, 100 nm, 150 nm, 200 nm, 250 nm, 300 nm, 400 nm, or 500 nm, or a size within a range bounded by any two of the foregoing values (e.g., 1-10 nm, 2-10 nm, 1-20 nm, 2-20 nm, 3-20 nm, 1-50 nm, 1-60 nm, 1-70 nm, 1-80 nm, 1-90 nm, 1-100 nm, 1-150 nm, or 5-150 nm). In one embodiment, the nanoparticles are fairly disperse in size (e.g., having a size variation of 20%, 30%, 40%, 50%, or greater from a median or mean size). In another embodiment, the nanoparticles are fairly monodisperse in size (e.g., having a size variation of or less than 50%, 40%, 30%, 20%, 10%, 5%, 2%, or 1% from a median or mean size).

The metal sulfide or metal selenide nanoparticles can also have any suitable morphology. Some examples of possible nanoparticle shapes include amorphous, fibrous, tubular, cylindrical, rod, needle, spherical, ovoid, pyramidal, cuboidal, rectangular, dodecahedral, octahedral, plate, and tetrahedral. In some embodiments, the metal sulfide or metal selenide nanoparticles are equiaxed euhedral crystals (i.e., typically cubes, octahedra, and modifications thereof). It is contemplated that one or more conditions, as provided above, could be controlled and tuned to produce nanoparticles having a desired composition or physical characteristic, such as amorphous vs. crystalline, or polycrystalline vs. single-crystalline, or polydisperse (in size) vs. fairly monodisperse in size.

Examples have been set forth below for the purpose of illustration and to describe certain specific embodiments of the invention. However, the scope of this invention is not to be in any way limited by the examples set forth herein.

EXAMPLES

Preparation and Characterization of ZnS Nanoparticles

Experimental Conditions

An anoxic sterile basal growth medium was used. The medium contained the following ingredients (g/L): 2.5 $NaHCO_3$, 0.08 $CaCl_2 \cdot 2H_2O$, 1.0 $NH_4Cl$, 0.2 $MgCl_2 \cdot 6H_2O$, 1-10.0 NaCl, 7.2 HEPES (hydroxyethylpiperazine-N'-2-ethanesulfonic acid), 0.5 yeast extract, 0.1 mL of 0.1% resazurin, 10 mL of trace minerals, and 1 mL of vitamin solutions. No exogenous electron carrier substance (i.e., anthraquinone disulfonate) or reducing agent (i.e., cysteine) was added to the anaerobic medium. The trace mineral solution contained (mg/L): 1500 Nitrilotriacetic acid, 200 $FeCl_2 \cdot 4H_2O$, 100 $MgCl_2 \cdot 6H_2O$, 20 sodium tungstate, 100

$MnCl_2 \cdot 4H_2O$, 100 $CoCl_2 \cdot 6H_2O$, 1000 $CaCl_2 \cdot 2H_2O$, 50 $ZnCl_2$, 2 $CuCl_2 \cdot 2H_2O$, 5$H_3BO_3$, 10 sodium molybdate, 1000 NaCl, 17 $Na_2SeO_3$, 24 $NiCl_2 \cdot 6H_2O$. The vitamin contained (g/L): 0.02 biotin, 0.02 folic acid, 0.1 B6 (pyridoxine) HCl, 0.05 B1 (thiamine) HCl, 0.05 B2 (riboflavin), 0.05 nicotinic acid (niacin), 0.05 pantothenic acid, 0.001 B12 (cyanocobalamin) crystalline, 0.05 PABA (P-aminobenzoic acid), and 0.05 lipoic acid (thioctic).

Various media can be used at an initial pH of about 8.0-8.2. FS medium was prepared by reducing the NaCl concentration from 10 to 1 g/L, removing 30 mM $NaHCO_3$, and titrating with 10 M NaOH to pH 8.2. FM medium was modified from FS medium by removing 7.2 g/L hydroxyethylpiperazine-N'-2-ethanesulfonic acid (HEPES) buffer, and titrating with 3-(N-morpholino) propanesulfonic acid sodium salt (MOPS) buffer to pH 8.2. FC medium contained no $NaHCO_3$ or organic buffers (HEPES or MOPS); it was titrated with 10 M NaOH to pH 8.2, and additional 10 M NaOH was added during fermentation to neutralize organic acids produced by the bacteria.

Figure 1:
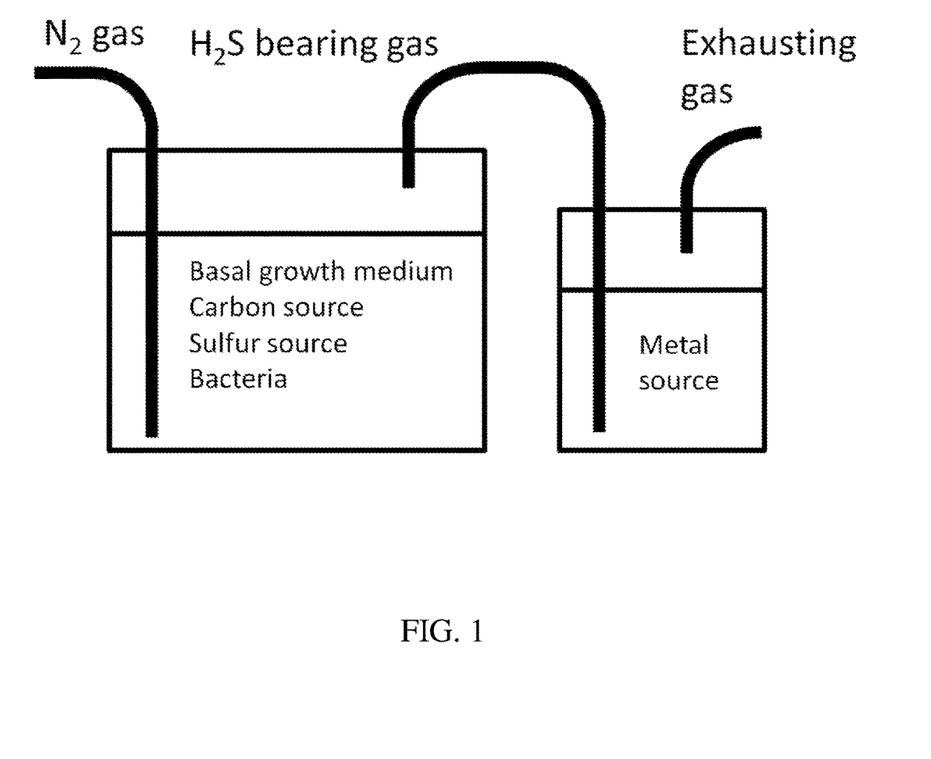
FIG. 1. A process diagram illustrating a preferred embodiment of the invention for preparing metal chalcogenide nanoparticles.

Culturing was initiated with carbon and sulfur sources and mid-log growth bacteria only. After the development of hydrosulfide ($HS^-$) in the solution and hydrogen sulfide ($H_2S$) gas in the headspace for more than 48 hours, nitrogen gas was used to sparge the primary reactor solution (microbial source for $H_2S$ production) and drive the $H_2S$-bearing gas into the 5 mM-1 M zinc acetate solution contained in a secondary reactor. A general schematic of the process is provided in FIG. 1.

Characterization of Nanoparticles

The produced nanoparticles were cleansed by repetitious centrifugation (11,700 g) and shaking on an end-to-end shaker in deionized water. Wet solid particles in water were switched into methanol slurry and the slurry was applied to a silica zero background plate for the phase identification using an X-ray diffractometer equipped with Mo-Ka radiation at 55 kV/40 mA between 5-35° 2θ with 1.5° 2θ/min. Average crystallite size (ACS) was determined from XRD results using the Scherrer equation after the peak breadths correction for instrumental broadening using a calibration curve based on $LaB_6$ powder data.

Fourier transform infrared (FTIR) spectroscopy measurements were conducted on the dry powders using a PIKE diamond crystal-attenuated total reflection on a FTIR spectrometer equipped with a deuterated triglycine sulfate detector, in the range of 600-4000 $cm^{-1}$. Carbon and nitrogen contents on the ZnS nanoparticle surface were determined after grinding a fine powder and oven-dry at 70° C. overnight. Approximately 0.2 g of ground sample was analyzed using an elemental analyzer. A standard of known carbon and nitrogen concentration (carbon=2.77%±0.06% SD, nitrogen=0.233%±0.013% SD) was used to ensure the accuracy and precision of the measurements.

Particle (aggregate) size determination (PSD) analysis by dynamic light scattering (DLS) used a ZetaPALS system. The ZnS samples were washed with deionized water followed by sonication using a 500-W, 3-mm tip-probe sonifier at 40 kHz for 5 to 30 minutes in an ice water bath prior to analysis.

The absorbance of the ZnS NPs was characterized using a UV/vis/NIR spectrometer, and photoluminescence (PL) was measured using a customized Hamamatsu system excited by a HeCd laser (325 nm). All measurements were conducted at room temperature.

Comparison Study Using Commercial $H_2S$ Gas

In separate experiments, to study the differences between ZnS nanoparticles produced from the claimed complementary NF (and conventional NF) process, commercial $H_2S$ gas (40 ppm balanced with $N_2$) was passed through 1M Zn-acetate solution in water with stirring. A completely abiotic closed system was studied with all conditions otherwise the same compared to the complementary NF process. Sparging was continued until complete consumption of the $H_2S$ (from a 33A cylinder) with stirring in the Zn-acetate solution.

X-Ray Diffraction (XRD) and Size Analysis of ZnS Particles

Figure 2:
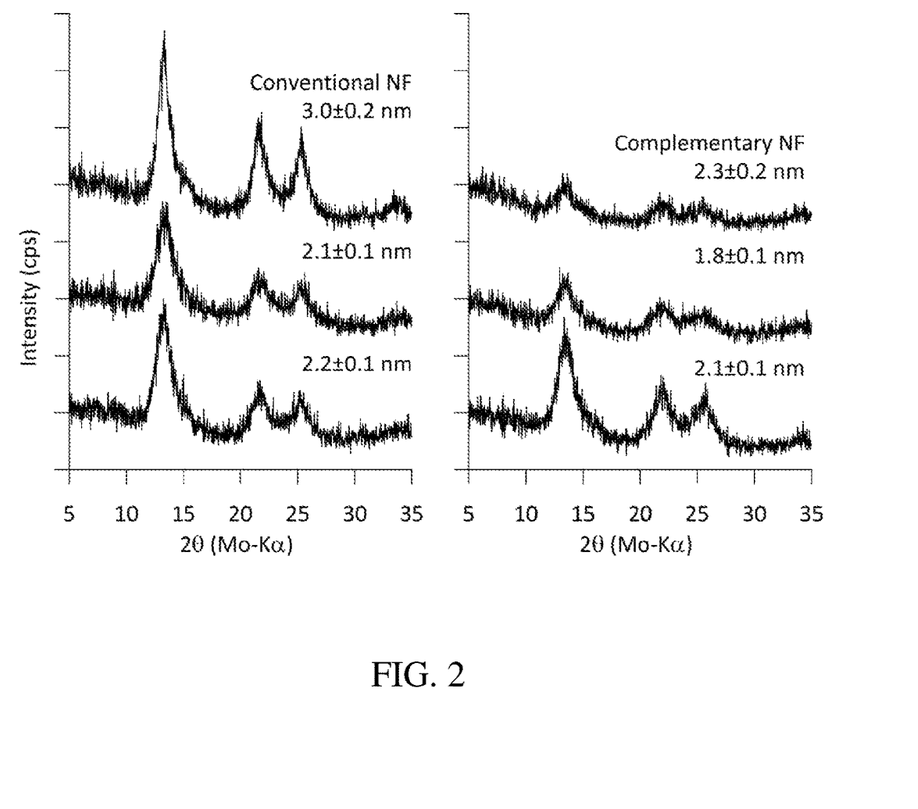
FIG. 2. Comparative XRD patterns for ZnS particles produced by the conventional nanofermentation (NF) process and by the novel process described herein (also termed "complementary nanofermentation" or "complementary NF"). The designations provided for each curve are defined in Table 1.

FIG. 2 provides comparative XRD patterns for ZnS particles produced by the conventional NF process and by the novel process described herein (also termed "complementary NF"). Correspondences for each designation provided for each curve are provided in Table 1 below.

TABLE 1

Average crystallite size (ACS) and yield from both conventional NanoFermentation (NF) and complementary NF.

| Sample Name | ACS | Description | Yield | Comment |
|---|---|---|---|---|
| *Conventional NF* | | | | |
| Q11047 | 3.0 ± 0.2 nm | FM medium in 900-L | 322 g | FY2015Q1 |
| Q10871 | 2.1 ± 0.1 nm | FeS medium in 100-L | 50.2 g | FY2014Q4 |
| Q10905 | 2.2 ± 0.1 nm | FeS medium in 100-L | 53.4 g | FY2014Q4 |
| *Complementary NF* | | | | |
| Q11061 | 2.3 ± 0.2 nm | 1M Zinc acetate in DI water | 40.5 g | FY2015Q2 |
| Q11062 | 2.0 ± 0.1 nm | 1M Zinc acetate in DI water | 9.17 g | FY2015Q2 |
| Q11063 | 1.9 ± 0.1 nm | 1M Zinc acetate in DI water | 13.8 g | FY2015Q2 |
| Q11064 | 1.8 ± 0.1 nm | 1M Zinc acetate in DI water | 21.5 g | FY2015Q2 |
| Q11148 | 2.1 ± 0.1 nm | 1M Zinc acetate in DI water | 52.7 g | FY2015Q2 |

As evident from FIG. 2 and Table 1 above, the ZnS products produced by complementary NF were comparable in many respects to those produced by the conventional NF technique. Based on the XRD patterns, the ACS values are very close for the two processes, at least when using FeS medium.

ZnS (6.4±0.3 nm) samples produced from the complementary NF process were suspended and 1-day samples and 7-day samples exhibited good suspension, even though there were some precipitation at the bottom. In contrast, CuS and SnS resulted in dominant aggregation and precipitation of CuS suspension after 1 minute and some SnS (6.0±0.4 nm) still suspended after 2 days. From these results, it is apparent that acetate appears suitable for the formation of fine nanoparticles of ZnS with minimal aggregation, but it was not as effective for CuS and SnS, especially CuS. Nevertheless, it is believed that precipitation in CuS and SnS could likely be substantially reduced by inclusion of suitable capping molecules during growth. Moreover, a large hump in the 2 theta 10~20 degree in the XRD of the CuS sample may indicate the presence of an amorphous phase, which may be related to the quick precipitation.

Figure 3:
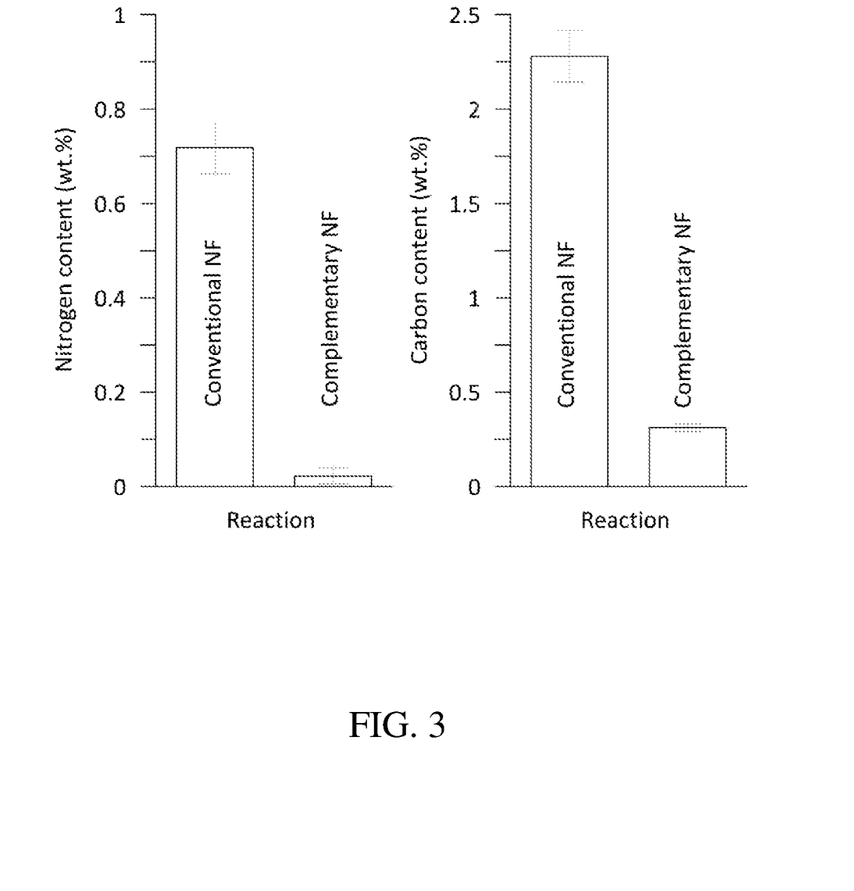
FIG. 3. Graphs showing total nitrogen and carbon analysis of ZnS particles produced by either complementary NF (of the present invention) or conventional NF.
Figure 4:
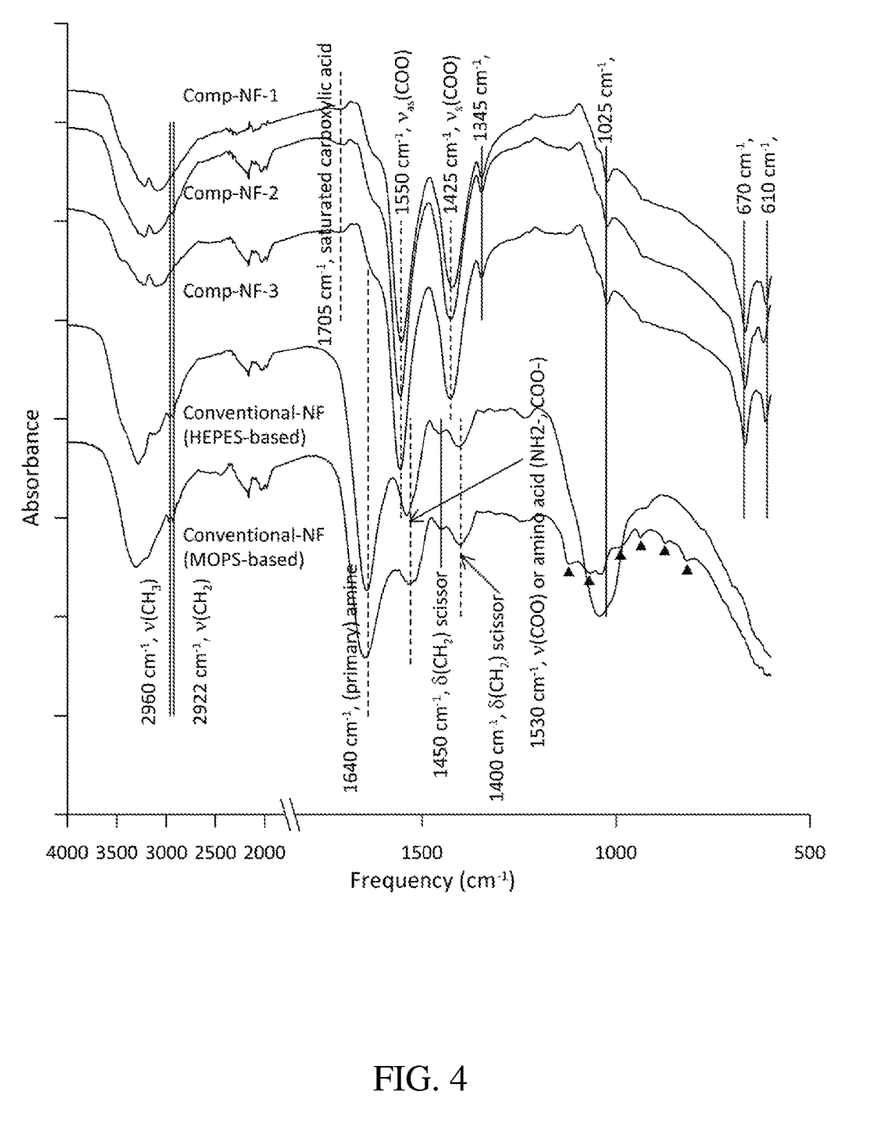
FIG. 4. FTIR spectra of ZnS particles produced by either complementary NF or conventional NF, to compare the surface coating compositions of each.

Three complementary NF ZnS samples were selected from Table 1 and their total nitrogen and carbon was analyzed using conventional soil analysis methods. These values were compared to previous NF samples with calibration of gamma $Al_2O_3$ reference material values. As shown from the plot of nitrogen and carbon analysis in FIG. 3, triplicates of complementary NF ZnS samples had lower nitrogen (0.017%) and carbon (0.308%) composition compared to conventional NF ZnS with nitrogen (0.718%) and carbon (2.28%). The new complementary NF process successfully reduced surface nitrogen and carbon contents in the final nanoparticles at a fraction of 2.3% (N) and 13% (C). Relatively less carbon amount was reduced but the surface should be mostly acetate. The results of FTIR analysis are provided in FIG. 4. As shown, ZnS particles produced by the complementary NF process exhibited a substantial removal of amine peak as compared to ZnS particles produced from the conventional samples. The ZnS particles produced by the complementary NF process also have more well-matched carboxylate peaks at 1425 $cm^{-1}$ and 1550 $cm^{-1}$. ZnS from conventional NF showed primary amine (1640 $cm^{-1}$) and shifted carboxylate peaks (1530 $cm^{-1}$ and 1450 $cm^{-1}$) that could easily be shifted by weak interactions, such as hydrogen bonding.

Figure 5:
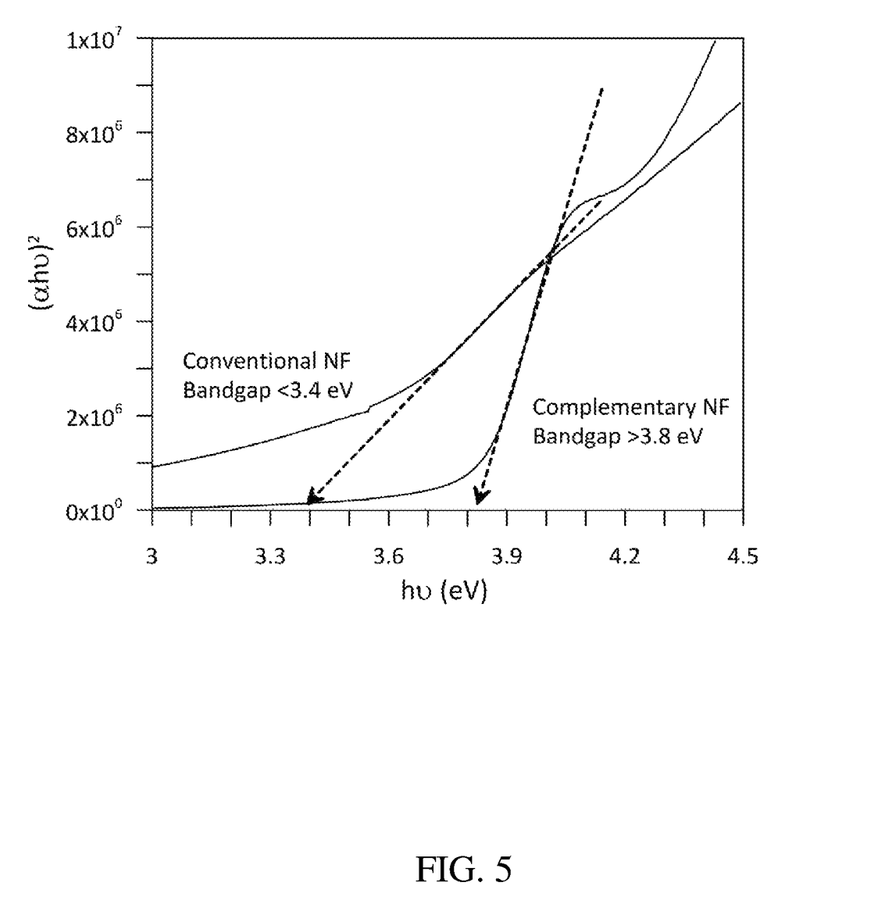
FIG. 5. Plot of optical properties and bandgap change for ZnS particles produced by either complementary NF or conventional NF.

Even though ZnS and SnS produced by complementary NF had similar average crystallite sizes of 6.47 nm and 6.5 nm, respectively, ZnS produced by complementary NF exhibited a crystallite size slightly larger than ZnS produced by conventional NF (2-3 nm). Yet, the ZnS suspension produced by complementary NF was fairly improved (i.e., more stable) compared to ZnS produced by conventional NF. The fact that the ZnS produced by complementary NF was well-dispersed but with larger ACS indicates that the ZnS produced by complementary NF did not aggregate to the extent normally encountered in the conventional NF. The foregoing results indicate that the ZnS particles produced by complementary NF have an effective (agglomerated) size that is likely significantly smaller than the 100-200 nm particle size typically produced by conventional NF. FIG. 5 compares the optical properties and bandgap changes for ZnS particles produced by either complementary or conventional NF. FIG. 5 shows enhanced optical properties and a blue-shifted bandgap from <3.4 eV to >3.8 eV, which indicates well-dispersed ZnS particles were produced by the complementary NF.

Not much of a difference in crystallite size was observed in ZnS particles produced by either complementary or conventional NF (both were in the range of about 2-7 nm). However, from an analysis of particle size distribution, it was found that the effective diameters of ZnS particles produced by abiotic means were 34 and 19 microns, which represent the effective sizes observed before and after sonication, respectively, during the measurement. Thus, surprisingly, the ZnS particles produced by abiotic means exhibited an approximately three-order magnitude larger effective particle size than ZnS particles produced by the complementary NF process described herein, even though both ZnS particles had similar average crystallite sizes. In other experiments, it was found that:

(i) a conventional NF process produced ZnS particles having an ACS of 1.9±0.1 nm and an effective diameter (from particle size distribution) of 3.63±3.93 microns;

(ii) the instant complementary NF process produced ZnS particles having an ACS of 1.9±0.1 nm and an effective diameter (from particle size distribution) of 53.3±0.9 nm;

(iii) a pH titration method produced ZnS particles having an ACS of 2.1±0.1 nm and an effective diameter (from particle size distribution) of 46.5±1.8 nm;

(iv) a sample of commercial ZnS had an ACS of 35.9±1.9 nm and an effective diameter (from particle size distribution) of 192±1.7 nm; and (v) an abiotic method using commercial $H_2S$ gas produced ZnS particles having an ACS of 2.1±0.1 nm and an effective diameter (from particle size distribution) of 20.0-34.2 microns.

While there have been shown and described what are at present considered the preferred embodiments of the invention, those skilled in the art may make various changes and modifications which remain within the scope of the invention defined by the appended claims.

What is claimed is:

1. A method for producing metal chalcogenide nanoparticles, the method comprising:
   (i) producing hydrogen chalcogenide-containing vapor from a microbial source, wherein said microbial source comprises: (a) chalcogen-reducing microbes capable of producing hydrogen chalcogenide vapor from a chalcogen-containing source; (b) a culture medium suitable for sustaining said chalcogen-reducing microbes; (c) at least one reducible chalcogen-containing compound that can be converted to hydrogen chalcogenide vapor by said chalcogen-reducing microbes; and (d) at least one nutritive compound that provides donatable electrons to said chalcogen-reducing microbes during consumption of the nutritive compound by said chalcogen-reducing microbes; and
   (ii) directing said hydrogen chalcogenide-containing vapor into a metal-containing solution comprising a metal salt dissolved in a solvent to produce metal chalcogenide nanoparticles in said solution;
wherein said chalcogen is sulfur or selenium, and said chalcogenide is sulfide or selenide, respectively.

2. The method of claim 1, wherein said metal chalcogenide nanoparticles have a secondary particle size of up to or less than 100 nm.

3. The method of claim 1, wherein the metal in said metal salt is one or more metals selected from the group consisting of transition metals and main group metals.

4. The method of claim 1, wherein the metal in said metal salt is one or more metals selected from the group consisting of Zn, Cu, Sn, Cd, Fe, Ga, In, Pb, and Hg.

5. The method of claim 1, wherein said reducible chalcogen-containing compound is a reducible sulfur-containing or selenium-containing compound and said chalcogen-reducing microbes are sulfur-reducing or selenium-reducing microbes, respectively.

6. The method of claim 5, wherein said reducible chalcogen-containing compound is a reducible sulfur-containing compound selected from the group consisting of sulfate, sulfite, elemental sulfur, thiosulfate, and organosulfur compounds, and said chalcogen-reducing microbes are sulfur-reducing microbes selected from the group consisting of sulfate-reducing, sulfite-reducing, elemental sulfur-reducing, organosulfur-reducing, and thiosulfate-reducing microbes.

7. The method of claim 5, wherein said reducible chalcogen-containing compound is a reducible selenium-containing compound selected from the group consisting of selenate, selenite, elemental selenium, selenosulfate, and organoselenium compounds, and said chalcogen-reducing microbes are selenium-reducing microbes selected from the group consisting of selenate-reducing, selenite-reducing, elemental selenium-reducing, organoselenium-reducing, and thioselenate-reducing microbes.

8. The method of claim 1 wherein said at least one nutritive compound is a compound that can be oxidatively consumed by the microbes, wherein said compound is selected from the group consisting of carboxylate-containing compounds, carbohydrates, and hydrogen gas.

9. The method of claim 8, wherein said at least one nutritive compound is a sugar compound that can be oxidatively consumed by the microbes.

10. The method of claim 1, wherein said chalcogen-reducing microbes are anaerobic microbes.

11. The method of claim 1, wherein said chalcogen-reducing microbes are thermophilic, mesophilic, psychrophilic, or psychrotolerant microbes.

12. The method of claim 1, wherein the method is conducted under substantially anoxic conditions.

13. The method of claim 1, wherein said solvent comprises water.

14. The method of claim 1, wherein said solvent comprises an organic solvent.

15. The method of claim 1, wherein said metal salt contains a single species of metal ions, which results in metal chalcogenide nanoparticles having a mono-metal chalcogenide composition.

16. The method of claim 15, wherein said metal salt contains a single species of metal ions selected from the group consisting of Zn, Cu, Sn, Cd, Fe, Ga, In, Pb, and Hg, to result in metal chalcogenide nanoparticles having a mono-metal chalcogenide composition selected from the group consisting of ZnX, CuX, $Cu_2X$, SnX, $SnX_2$, CdX, FeX, $Fe_2X_3$, $Ga_2X_3$, $In_2X_3$, PbX, and HgX, wherein X is S or Se or a combination thereof.

17. The method of claim 1, wherein said metal salt contains at least two species of metal ions, which results in metal chalcogenide nanoparticles having a multi-metal chalcogenide composition.

18. The method of claim 17, wherein said metal salt contains at least two species of metal ions selected from the group consisting of Zn, Cu, Sn, Cd, Fe, Ga, In, Pb, and Hg, to result in metal chalcogenide nanoparticles having a multi-metal chalcogenide composition containing at least two of said species of metal ions.

19. The method of claim 18, wherein said metal salt contains at least Cu, In, and Ga metal ions, to result in a CIGS-type composition according to the formula:

$$Cu(In_xGa_{1-x})X_2 \qquad (1)$$

wherein x is an integral or non-integral numerical value of or greater than 0 and less than or equal to 1, and X represents S, Se, or a combination thereof.

20. The method of claim 18, wherein said metal salt contains at least Sn metal ions and at least one other species of metal ion selected from Cu, Fe, Zn, and Cd, to result in a kesterite-type composition according to the formula:

$$MSnX_4 \qquad (2)$$

wherein M represents at least one metal ion selected from Cu, Fe, Zn, and Cd, and X represents S, Se, or a combination thereof.

21. The method of claim 20, wherein said metal salt contains at least Sn and Cu metal ions and at least one other species of metal ion selected from Fe, Zn, and Cd, to result in a kesterite-type composition according to the formula:

$$Cu_{3-x}M'_xSnX_4 \qquad (2a)$$

wherein M' represents at least one metal ion selected from Fe, Zn, and Cd, and X represents S, Se, or a combination thereof.

* * * * *